United States Patent
Nakagami et al.

(10) Patent No.: US 6,335,036 B1
(45) Date of Patent: *Jan. 1, 2002

(54) GRANULAR PHARMACEUTICAL PREPARATION OF EBSELEN

(75) Inventors: Hiroaki Nakagami; Taketoshi Keshikawa, both of Tokyo (JP)

(73) Assignee: Daiichi Pharmaceutical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/635,880

(22) PCT Filed: Oct. 27, 1993

(86) PCT No.: PCT/JP93/01553

§ 371 Date: Apr. 23, 1996

§ 102(e) Date: Apr. 23, 1996

(87) PCT Pub. No.: WO95/11674

PCT Pub. Date: May 4, 1995

(51) Int. Cl.⁷ .......................... A61K 9/16; A61K 31/41
(52) U.S. Cl. ........................ 424/489; 514/360; 548/121
(58) Field of Search ................................. 424/244, 245, 424/489; 514/360; 548/121

(56) References Cited

U.S. PATENT DOCUMENTS

| | | | | |
|---|---|---|---|---|
| 4,352,799 A | * | 10/1982 | Renson et al. | 424/167 |
| 4,606,909 A | * | 8/1986 | Bechgaard et al. | |
| 4,778,814 A | * | 10/1988 | Cash | |
| 4,784,994 A | * | 11/1988 | Romer et al. | |
| 5,008,394 A | * | 4/1991 | Günther et al. | |
| 5,021,242 A | * | 6/1991 | Börner et al. | |
| 5,288,734 A | * | 2/1994 | Hager et al. | |
| 5,385,726 A | * | 1/1995 | Balden et al. | |
| 5,948,800 A | * | 9/1999 | Maruyama et al. | |

FOREIGN PATENT DOCUMENTS

| | | | |
|---|---|---|---|
| DE | 3226284 | 1/1984 | |
| DE | 3407511 | 9/1985 | |
| DE | 4024885 | 2/1992 | |
| DE | 4109508 | 6/1992 | |
| EP | 0044453 | 1/1982 | |
| EP | 0044971 | 2/1982 | |
| EP | 0249735 | 12/1987 | |
| EP | 0347927 | 12/1989 | |
| JP | 59-42313 | * 3/1984 | ............ A61K/9/70 |
| JP | 63027431 | 5/1988 | |
| JP | 1-100125 | * 4/1989 | ......... A61K/31/555 |
| JP | 0113522 | 5/1989 | |

* cited by examiner

Primary Examiner—Edward J. Webman
(74) Attorney, Agent, or Firm—Sughrue Mion, PLLC

(57) ABSTRACT

A granular pharmaceutical preparation prepared by granulating finely powdered Ebselen(2-phenyl-1,2-benzisoselenazol-3(2H)-one) using a hydrophilic polymer, and an aqueous suspension thereof. The Ebselen granular pharmaceutical preparation of the present invention is excellent in its performance as an oral preparation for use in stomach tube administration. That is, since it can be dispersed easily and uniformly when suspended in water or an aqueous solution before its use, and the suspension can be maintained in excellent dispersed state, preparation and tube administration of the drug solution can be made easily. Also, its dose is accurate because the administration can be effected with no drug or drug solution remained in the tube after the administration. In addition, the granular pharmaceutical preparation of the present invention is also suited for its large scale production, because it can be produced without employing special apparatuses and production steps.

8 Claims, No Drawings

GRANULAR PHARMACEUTICAL PREPARATION OF EBSELEN

TECHNICAL FIELD

This invention relates to granular pharmaceutical preparations and aqueous suspensions of Ebselen (2-phenyl-1,2-benzisoselenazol-3(2H)-one) which is an antioxidant used as a medicine and, more particularly, a granular pharmaceutical preparation of Ebselen which can be dispersed easily in water before using, shows excellent suspension stability and can be administered through a stomach tube or a stomach catheter to patients of subarachnoid hemorrhage and the like who cannot be treated by oral administration, and an aqueous suspension which is obtained by mixing the preparation with water or an aqueous solution.

BACKGROUND ART

Only injections are available hitherto as therapeutic drugs for patients of subarachnoid hemorrhage and the like who cannot take oral preparations. However, administration of drugs by injection has problems in that it gives patients pain and uneasiness at the time of injection, it requires strict sterility, it is apt to cause intoxication and side effect and there are almost no means for detoxication when a medicating mistake is made.

On the other hand, tube administration is carried out using a stomach tube when it is necessary to apply an oral preparation to a patient who cannot take the oral preparation.

Ebselen is known as a compound which shows excellent antioxidation function in the living body, but having problems in that it has poor water dispersibility because it is hardly water-wettable and slightly soluble in water due to its hydrophobic nature, and the solid matter separates immediately after dispersion and floats or precipitates because of its poor suspension stability. In consequence, even if Ebselen is made into granules or fine subtilaes, application of such preparations to the aforementioned tube administration is difficult or impossible because the solid matter remains in the stomach tube or, at the worst, blocks up the tube.

In general, a surface active agent is used to improve dispersibility of such hydrophobic drugs, and a suspending agent such as sodium carboxymethyl cellulose, acasia or the like is used to improve suspension stability. However, usable kinds and amounts of these agents are limited, because the former has a problem in view of safety and the latter has another problem in that it can be used in suspensions for internal use making use of its viscosity-increasing property, but such a viscosity-increasing property conversely exerts serious influences upon production aptitude, safety and bioavailability when used in solid preparations.

In consequence, great concern has been directed toward the development of a granular pharmaceutical preparation of Ebselen which does not contain surface active agents and suspending agents, can be dispersed in water easily and has excellent suspension stability.

DISCLOSURE OF THE INVENTION

Taking such actual circumstances into consideration, the inventors of the present invention have conducted extensive studies investigations and as a result, found that a granular pharmaceutical preparation which disperses easily in water or an aqueous solution and has excellent suspension stability can be obtained by granulating Ebselen having a particle size equal to or smaller than a specified size making use of a hydrophilic polymer, thus resulting in the accomplishment of the present invention.

Accordingly, an object of the present invention is to provide a granular pharmaceutical preparation obtained by granulating finely powdered Ebselen making use of a hydrophilic polymer and an aqueous suspension which contains finely powdered Ebselen and a hydrophilic polymer.

Another object of the present invention is to provide a granular pharmaceutical preparation having an average particle size of from 50 to 2,000 gm which is obtained by granulating finely powdered Ebselen having an average particle size of 50 $\mu$m or less, preferably 10 $\mu$m or less, making use of a hydrophilic polymer.

Still another object of the present invention is to provide the above granular pharmaceutical preparation in which the hydrophilic polymer is used in an amount of from 0.5 to 100% by weight based on Ebselen.

A further object of the present invention is to provide an aqueous suspension prepared by suspending the above granular pharmaceutical preparation in water or an aqueous solution.

Finely powdered Ebselen to be used in the present invention may be obtained with no particular limitation, for example, by using a grinder such as a jet mill, a ball mill or the like, or by employing a quick precipitation method in which a temperature or a solvent composition is changed rapidly. The finely powdered Ebselen to be used in the present invention may have an average particle size of generally 50 $\mu$m or less, preferably 10 $\mu$m or less. In this instance, the average particle size as used herein means a value measured by a laser diffraction particle size distribution measuring apparatus. The amount of the finely powdered Ebselen blended in the granular pharmaceutical preparation of the present invention can be changed depending on the disease to be treated by the administration of the preparation, but may be generally in the range of from 10 to 50% by weight.

The hydrophilic polymer to be used in the present invention is not particularly limited, provided that it is used generally as a binder, with its illustrative examples including hydroxypropylmethyl cellulose, hydroxypropyl cellulose, methyl cellulose, polyvinyl alcohol, polyvinyl pyrrolidone, gelatin and the like, all of which can be obtained from commercial sources with no particular limitation on their particle sizes. The blending amount of the hydrophilic polymer in the granular pharmaceutical preparation of the present invention may be selected optionally depending on the amount of Ebselen to be blended, type of the hydrophilic polymer, granulation method and the like, but generally in the range of from 0.5 to 100% by weight based on the amount of Ebselen.

In addition to the essential components Ebselen and hydrophilic polymer, the granular pharmaceutical preparation of the present invention may be further blended with fillers such as corn starch, lactose and the like, fluidizing agents such as talc, soft silicic anhydride and the like and disintegrating agents such as low substitution degree hydroxypropyl cellulose, calcium carboxymethyl cellulose and the like. The kind and amount of the filler blended are not particularly limited, the fluidizing agent may be used generally in an amount of from 0.1 to 5% by weight based on the whole composition, the disintegrating agent may be used generally in an amount of from 1 to 10% by weight based on the whole composition, and particle sizes of these additives are not particularly limited so that any commercially available agent (generally having an average particle size of from about 7 nm to about 50 $\mu$m) can be used.

The granular pharmaceutical preparation of the present invention can be produced by a wet granulation method such as extrusion granulation, rolling granulation, cracking granulation, fluidized bed granulation, spray granulation or the like, thereby making it into fine subtilaes, granules and the like granular forms. Fine subtilaes or granules may be produced, for example, by mixing Ebselen uniformly with other additive agents, adding aqueous solution of a hydrophilic polymer to the mixture, subjecting the resulting mixture to granulation by the aforementioned means and then subjecting the thus obtained granules to drying and subsequent grading. The concentration of a hydrophilic polymer in the above described aqueous solution varies depending on the type of the hydrophilic polymer to be used, and, in the case of hydroxypropyl cellulose, for example, its concentration may be generally 10% (w/v) or less. Though not particularly limited, the thus obtained granular pharmaceutical preparation may have a particle size in the range of preferably from 50 to 2,000 µm, more preferably from 70 to 1,000 µm.

An aqueous suspension can be obtained by adding water or an aqueous solution to the thus obtained granular pharmaceutical preparation, and its viscosity can be changed depending on the administration rate, dose and the like at the time of the administration of the preparation, which may be generally within the range of from 1 to 30 centi poises though it varies depending on the content of the hydrophilic polymer contained in the granular pharmaceutical preparation. Examples of the aforementioned aqueous solution include physiological saline, phosphate buffer and the like.

BEST MODE OF CARRYING OUT THE INVENTION

The following examples are provided to further illustrate the present invention, though these examples are not intended as a definition of the limits of the invention.

INVENTIVE EXAMPLE 1

A 7.5 g portion of hydroxypropyl cellulose (hereinafter referred to as "HPC") was dissolved in water in advance and the total volume of the solution was adjusted to 150 ml to prepare an HPC binder solution. A fluidized bed granulating machine was charged with 100 g of Ebselen having an average particle size of 2.7 µm, 100 g of lactose (average particle size, about 10 µm) and 2 g of soft silicic anhydride (primary average particle size, about 7 nm), and granulation was effected by spraying the HPC binder solution. After completion of the granulation, grading was carried out using a No. 30 screen (nominal size, 500 µm), and granules on the screen (portions not passed through the screen) were ground on a mortar and again subjected to grading to obtain a fine subtilae preparation of Ebselen (particle size, 500 µm or less).

INVENTIVE EXAMPLE 2

A 10.0 g portion of HPC was dissolved in water in advance and the total volume of the solution was adjusted to 200 ml to prepare an HPC binder solution. A fluidized bed granulating machine was charged with 100 g of Ebselen having an average particle size of 2.7 µm, 100 g of lactose (average particle size, about 10 µm) and 2 g of soft silicic anhydride (primary average particle size, about 7 nm), and granulation was effected by spraying the HPC binder solution. After completion of the granulation, grading was carried out using a No. 30 screen, and granules on the screen were ground on a mortar and again subjected to grading to obtain a fine subtilae preparation of Ebselen.

INVENTIVE EXAMPLE 3

A 10.0 g portion of hydroxypropylmethyl cellulose (hereinafter referred to as "HPMC"; viscosity grade, 15 cps) was dissolved in water in advance and the total volume of the solution was adjusted to 200 ml to prepare an HPMC binder solution. A fluidized bed granulating machine was charged with 100 g of Ebselen having an average particle size of 2.7 µm, 100 g of lactose (average particle size, about 10 µm) and 2 g of soft silicic anhydride (primary average particle size, about 7 nm), and granulation was effected by spraying the HPMC binder solution. After completion of the granulation, grading was carried out using a No. 30 screen, and granules on the screen were ground on a mortar and again subjected to grading to obtain a fine subtilae preparation of Ebselen.

INVENTIVE EXAMPLE 4

A 10.0 g portion of polyvinyl alcohol (hereinafter referred to as "PVA") was dissolved in water in advance and the total volume of the solution was adjusted to 200 ml to prepare a PVA binder solution. A fluidized bed granulating machine was charged with 100 g of Ebselen having an average particle size of 2.7 µm, 100 g of lactose (average particle size, about 10 µm) and 2 g of soft silicic anhydride (primary average particle size, about 7 nm), and granulation was effected by spraying the PVA binder solution. After completion of the granulation, grading was carried out using a No. 30 screen, and granules on the screen were ground on a mortar and again subjected to grading to obtain a fine subtilae preparation of Ebselen.

COMPARATIVE EXAMPLE 1

A 100 g portion of Ebselen having an average particle size of 2.7 µm was uniformly mixed with 10.0 g of HPC, 100 g of lactose (average particle size, about 10 µm) and 2 g of soft silicic anhydride (primary average particle size, about 7 nm).

COMPARATIVE EXAMPLE 2

A 10.0 g portion of HPC was dissolved in water in advance and the total volume of the solution was adjusted to 200 ml to prepare an HPC binder solution. A fluidized bed granulating machine was charged with 100 g of not particularly powdered Ebselen having an average particle size of 81 µm, 100 g of lactose (average particle size, about 10 µm) and 2 g of soft silicic anhydride (primary average particle size, about 7 nm), and granulation was effected by spraying the HPC binder solution. After completion of the granulation, grading was carried out using a No. 30 screen, and granules on the screen were ground on a mortar and again subjected to grading to obtain a fine subtilae preparation of Ebselen.

TEST EXAMPLE

A 2.5 g portion of each of the granular and powder pharmaceutical preparations obtained in Inventive Examples 1 to 4 and Comparative Examples 1 and 2 was weighed and put in a stoppered test tube and thoroughly mixed with 50 ml of water by shaking, and the thus obtained aqueous suspension was observed by the naked eye while periodically measuring the amount of powder precipitated in the test tube bottom as a distance between the tube bottom and the upper surface of the precipitate. The results are shown in Table 1 below.

TABLE 1

| Aqueous suspension | Just after Shaking | \multicolumn{5}{c}{Elapse of Time} |
|---|---|---|---|---|---|---|
| | | 10 min | 30 min | 1 hr | 2 hrs | 3 hrs |
| Inventive Example 1 | uniform milk white emulsion | 1 mm (milk white) | 1.5 mm (milk white) | 2 mm (milk white) | 2 mm (milk white) | 2 mm (milk white) |
| Inventive Example 2 | uniform milk white emulsion | 0.5 mm (milk white) | 1 mm (milk white) | 1.5 mm (milk white) | 1.8 mm (milk white) | 2 mm (milk white) |
| Inventive Example 3 | uniform milk white emulsion | 0.5 mm (milk white) | 1 mm (milk white) | 1.6 mm (milk white) | 2 mm (milk white) | 2.5 mm (milk white) |
| Inventive Example 4 | uniform milk white emulsion | 0.5 mm (milk white) | 1.2 mm (milk white) | 2 mm (milk white) | 2 mm (milk white) | 2.5 mm (milk white) |
| Comparative Example 1 | floating of powder, no suspension | — | — | — | — | — |
| Comparative Example 2 | partial floating of powder | 16 mm (almost clear) | 16 mm (almost clear) | 15 mm (almost clear) | 14 mm (almost clear) | 15 mm (almost clear) |

Note: Parentheses show results of the visual observation of conditions of aqueous suspensions.

As is evident from the results shown in Table 1, a mixture prepared without employing granulation and grading (Comparative Example 1) cannot be suspended due to floating of the powder, and a preparation granulated with a hydrophilic polymer using Ebselen having large particle size (Comparative Example 2) cannot be suspended due to precipitation of Ebselen, thus indicating that they are unpractical as preparations for tube administration use. On the contrary, each of the granular pharmaceutical preparations produced by adding a hydrophilic polymer to finely powdered Ebselen in accordance with the present invention (Inventive Examples 1 to 4) is easily dispersible in water and has excellent suspension stability.

INDUSTRIAL APPLICABILITY

The granular pharmaceutical preparation of the present invention is excellent in its performance as a preparation for use in tube administration. That is, since it can be dispersed easily and uniformly when suspended in water or an aqueous solution before its use, and the suspension can be maintained in excellent dispersed state, preparation and tube administration of the drug solution can be made easily. Also, its dose is accurate because the administration can be effected with no drug or drug solution remained in the tube after the administration. In addition, the granular pharmaceutical preparation of the present invention is also suited for its large scale production, because it can be produced without employing special apparatuses and production steps.

What is claimed is:

1. A granular pharmaceutical preparation prepared by granulating finely powdered Ebselen (2-phenyl-1,2-benzisoselenazol-3(2H)-one) in the presence of an aqueous solution of a hydrophilic polymer, wherein the finely powdered Ebselen has an average particle size of 50 $\mu$m or less.

2. An aqueous suspension comprising a granular pharmaceutical preparation prepared by first granulating finely powdered Ebselen (2-phenyl-1,2-benzisoselenazol-3(2H)-one) in the presence of an aqueous solution of a hydrophilic polymer, wherein the finely powdered Ebselen has an average particle size of 50 $\mu$m or less, and then dispersing said preparation in water or an aqueous solution.

3. The granular pharmaceutical preparation according to claim 1, wherein said finely powdered Ebselen has an average particle size of 10 $\mu$m or less.

4. The granular pharmaceutical preparation according to claim 1 or 3, wherein said granular pharmaceutical preparation has a particle size of from 50 to 2,000 $\mu$m.

5. The granular pharmaceutical preparation according to claim 4, wherein said hydrophilic polymer is used in an amount of from 0.5 to 100% by weight based on Ebselen.

6. The aqueous suspension according to claim 2, wherein said finely powdered Ebselen has an average particle size of 10 $\mu$m or less.

7. The aqueous suspension according to claim 2 or 6, wherein said granular pharmaceutical preparation has a particle size of 50 to 2,000 $\mu$m.

8. The aqueous suspension according to claim 7, wherein said hydrophilic polymer is used in an amount of from 0.5 to 100% by weight based on Ebselen.

* * * * *